(12) United States Patent
Khodadadyan-Klostermann et al.

(10) Patent No.: US 7,985,223 B2
(45) Date of Patent: Jul. 26, 2011

(54) VENTRAL BONE PLATE

(75) Inventors: Cyrus Khodadadyan-Klostermann, Berlin (DE); Carsten Neumann, Bad Abbach (DE)

(73) Assignee: Ulrich GmbH + Co. KG, Ulm (DE)

( * ) Notice: Subject to any disclaimer, the term of this patent is extended or adjusted under 35 U.S.C. 154(b) by 760 days.

(21) Appl. No.: 11/519,452

(22) Filed: Sep. 12, 2006

(65) Prior Publication Data

US 2007/0093838 A1 Apr. 26, 2007

(30) Foreign Application Priority Data

Sep. 16, 2005 (DE) .......................... 10 2005 044 532

(51) Int. Cl.
*A61B 17/80* (2006.01)

(52) U.S. Cl. .......................................... 606/71; 606/252

(58) Field of Classification Search .................. 606/70, 606/71, 280–299, 254–263, 86 B, 90, 105
See application file for complete search history.

(56) References Cited

U.S. PATENT DOCUMENTS

| | | | | |
|---|---|---|---|---|
| 4,836,196 A | * | 6/1989 | Park et al. ....................... | 606/246 |
| 5,092,893 A | * | 3/1992 | Smith ............................ | 606/290 |
| 5,108,395 A | * | 4/1992 | Laurain ........................ | 606/86 B |
| 6,315,779 B1 | * | 11/2001 | Morrison et al. .............. | 606/281 |
| 6,506,191 B1 | * | 1/2003 | Joos ............................. | 606/86 B |
| 6,569,164 B1 | * | 5/2003 | Assaker et al. ................ | 606/250 |
| 6,585,738 B1 | * | 7/2003 | Mangione et al. ............. | 606/258 |
| 6,645,208 B2 | * | 11/2003 | Apfelbaum et al. ............ | 606/71 |
| 6,872,210 B2 | * | 3/2005 | Hearn ............................. | 606/71 |
| 7,175,624 B2 | * | 2/2007 | Konieczynski et al. ........ | 606/71 |
| 2003/0171752 A1 | * | 9/2003 | Assaker et al. .................. | 606/61 |
| 2004/0122431 A1 | * | 6/2004 | Biedermann et al. ........... | 606/73 |
| 2005/0143737 A1 | * | 6/2005 | Pafford et al. .................. | 606/61 |
| 2005/0177161 A1 | | 8/2005 | Baynham ........................ | 606/69 |

FOREIGN PATENT DOCUMENTS

| EP | 689799 A1 * | 1/1996 |
|---|---|---|
| EP | 1 121 903 | 8/2001 |

OTHER PUBLICATIONS bight. (n.d.). Dictionary.com Unabridged (v 1.1). Retrieved Sep. 28, 2009, from Dictionary.com website: http://dictionary.reference.com/browse/bight.*

* cited by examiner

*Primary Examiner* — Eduardo C Robert
*Assistant Examiner* — Steven Cotroneo
(74) *Attorney, Agent, or Firm* — Andrew Wilford

(57) ABSTRACT

A ventral bone-plate assembly has a U-shaped base having a pair of legs bridged by a bight and each formed with an inner hole and an outer hole. A brace bar extends between outer ends of the legs and is formed with end holes alignable with the outer holes. Respective inner bone screws extend through the inner holes, and respective outer bone screws each extend through a respective one of the outer holes and a respective one of the end holes.

9 Claims, 7 Drawing Sheets

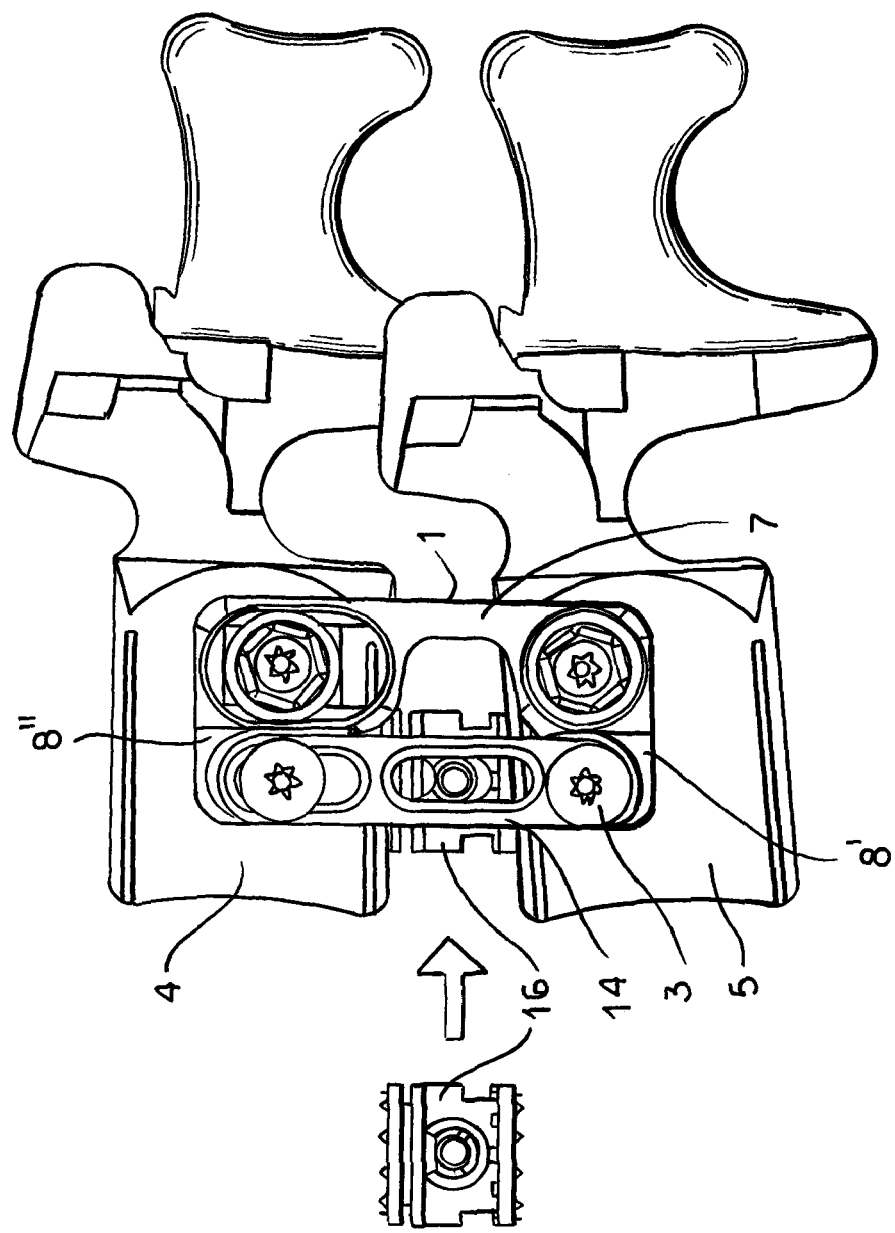

VENTRAL BONE PLATE

FIELD OF THE INVENTION

The present invention relates to a ventral plate. More particularly this invention concerns such a plate that is secured to two vertebras to stabilize a spine.

BACKGROUND OF THE INVENTION

A typical such ventral plate is formed with a plurality of holes for receiving bone screws that pass through the holes and that are to be screwed into the vertebral bodies of adjacent vertebras.

Bone plates for osteosynthesis have been known for a long time and are employed in particular in order to cover sites of fractures. Moreover, they are also employed in surgery on the spinal column for stiffening adjacent vertebral bodies. However, it is disadvantageous that with the known bone plates the surgeon cannot see the areas covered by the plate, which is particularly disadvantageous in spinal column surgery when, after the plate has been placed, the surgery must be continued for adding bone, bone cement, or another substitute element for the spinal column.

It has been suggested in U.S. Pat. No. 6,585,738 of Mangione and EP 1,121,903 of Calisse to use an L-shaped or U-shaped bone plate, but such a structure is often insufficiently strong. The bone plate, which is secured at each end by two screws, is subjected to considerable stress and failure could result in a serious spinal injury.

OBJECTS OF THE INVENTION

It is therefore an object of the present invention to provide an improved ventral bone plate.

Another object is the provision of such an improved ventral bone plate that overcomes the above-given disadvantages, in particular that does not block the surgeon's view of the surgical site, but that nonetheless is very strong once installed.

SUMMARY OF THE INVENTION

A ventral bone-plate assembly has according to the invention a U-shaped base having a pair of legs bridged by a bight and each formed with an inner hole and an outer hole. A separate brace bar extends between outer ends of the legs and is formed with end holes alignable with the outer holes. Respective inner bone screws extend through the inner holes and respective outer bone screws each extend through a respective one of the outer holes and a respective one of the end holes.

Such a configuration has the advantage that although it is possible to fix the plate to adjacent vertebral bodies using the bone screws that pass through the holes, the area between the vertebral bodies remains open and accessible because the area immediately between the legs of the base is left open. The legs provide a generously dimensioned positioning surface for the plate on the vertebral bodies so that forces can be transmitted without overstressing individual points.

In order to attain improved placement of the plate during ventral positioning on the vertebral bodies, the inner face on the side bearing on the vertebras is concave. Correct positioning of the plate relative to the vertebral bodies and any bone screws that are already inserted is assured when an oblong hole as well as a circular hole are formed in bight region of the base. This makes it possible not only to attach the ventral plate to the vertebral body using bones screws that pass through the holes, but additionally also to fix the base, it then being advantageous when the base and the legs are formed as two parts.

More particularly one of the legs of the base is actually formed by an insert slidable on the base toward and away form the other leg for length adjustment of the plate assembly. Thus for instance first the base or the legs are attached to the vertebral bodies in order thereafter to connect to the complementary component and assure its correct alignment. Naturally it is also still possible alternatively to attach the plate preassembled as a unit. For piece-by-piece attachment, it is advantageous when seats for the legs are formed in the base in order to ensure that the base and the insert hold together, even before the bone screws have been completely tightened. The displaceability desired and assured by the slot is retained even when such seats are used and formed if locking strips are formed in the slot extending in its longitudinal direction for interacting with locking tabs formed on the leg.

It is furthermore advantageous when two holes are formed on each leg because in this manner the second hole also makes it possible for the bone screw that passes through the slot or the circular hole to fix the leg relative to the base and relative to the vertebral body simultaneously.

The brace plate ensures that the space between the legs initially provides accessibility to the space behind the plate. The brace plate, which can be attached to the plate at a later time when accessibility is no longer required, changes the base's mechanical properties, in particular increasing its stiffness and resilience. A better, in particular positive-fit connection between the plate and the brace plate is attained in that seats are formed in the legs for positioning the brace plate.

So as not to have to provide any additional bone screws for the brace plate, the brace plate is formed with holes that align with the outer holes of the base holes when the brace plate is placed in the seats. In this case, it is particularly preferred when the holes on the side facing the vertebra are concave, since this provides the opportunity to orient the bone screws, in particular to modify the orientation of their longitudinal axis to the plate and to adapt it to the actual anatomical situation.

It is furthermore advantageous when the screws are present in two configurations, of which one has a convex screw head and the other has an annular collar on the screw head.

BRIEF DESCRIPTION OF THE DRAWING

The above and other objects, features, and advantages will become more readily apparent from the following description, reference being made to the accompanying drawing in which:

FIG. 11 is a view like FIG. 10 but showing the installation of a distractor.

SPECIFIC DESCRIPTION

Figure 3:
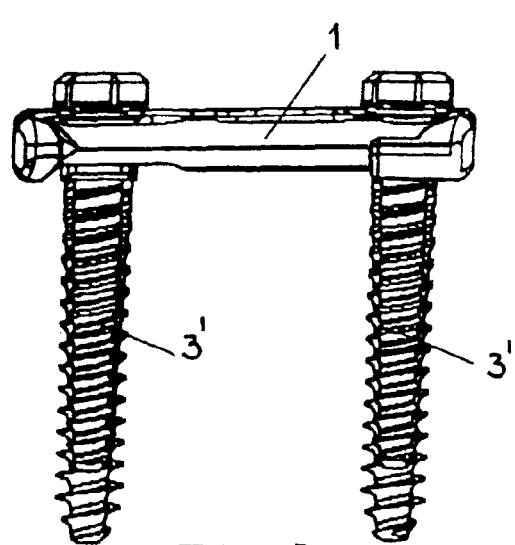
FIGS. 3, 4, and 5 are front, side, and top views of the assembly.
Figure 4:
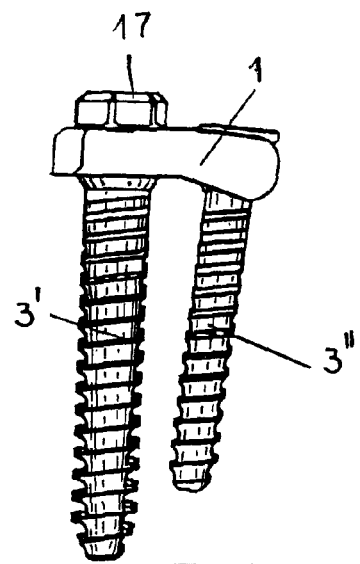
Figure 1:
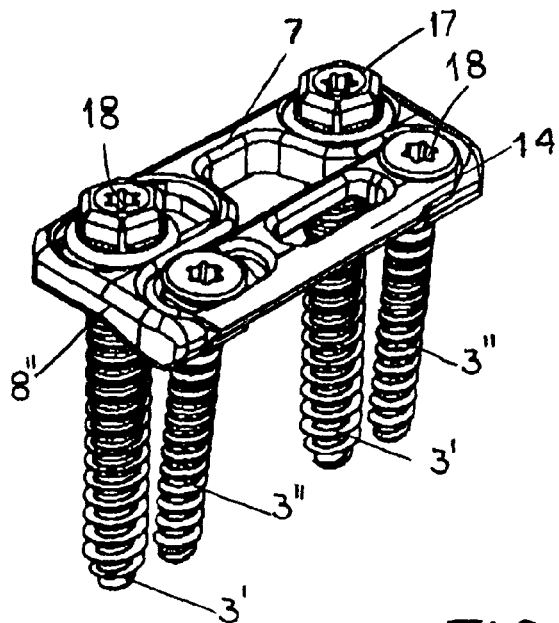
FIG. 1 is a perspective view of the bone plate according to the invention.

As seen in FIGS. 1-10 a ventral-plate assembly 1 that stabilizes the spinal column and has a plurality of holes 2, 9, and 10 through which pass bone screws 3' and 3" in order to attach the plate assembly 1 to bodies 4 (FIGS. 9-11) of adjacent vertebras. The bone screws 3' and 3" are of two types, one of which has a raised screw head 17 and the other has an frustoconical flat head 5 (see FIG. 2). The heads 5 and 17 are both formed with a central drive socket 18.

The plate assembly 1 has a U-shaped plate body 6 with a bight portion 7 and two legs 8' and 8" extending therefrom in whose inner ends are formed holes 9 and 10 for the bone screws 3' and in whose outer ends are formed circular-section holes 2 for the screws 3". The inner face of the plate assembly 1 that sits against the vertebral body 4 has a concave shape.

Figure 2:
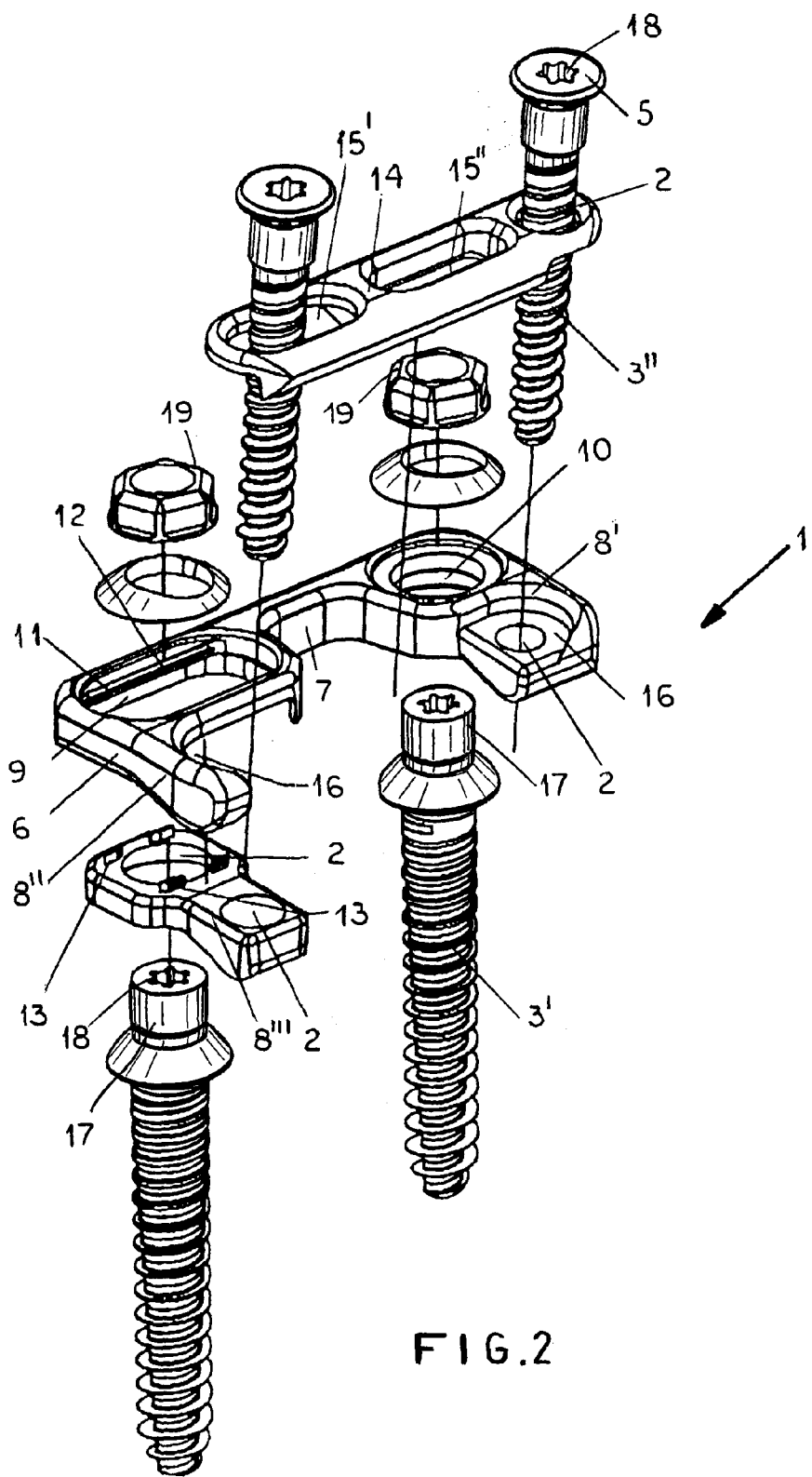
FIG. 2 is an exploded view of the entire bone-plate assembly.
Figure 5:
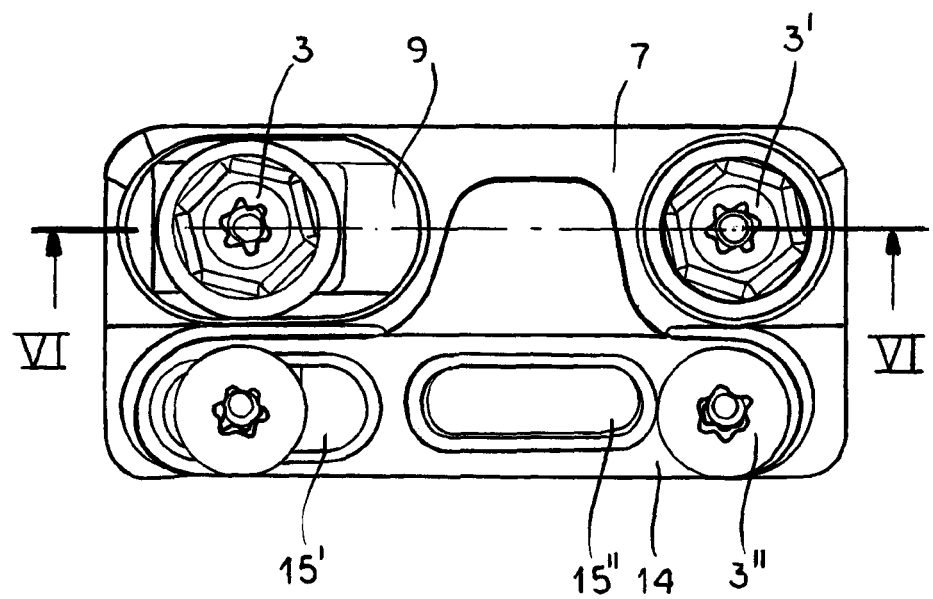

As can be seen in particular in FIG. 2, the hole 9 formed at the bight is actually an oblong slot and the other hole 10 is of circular shape. The slot 9 extends in a line aligned with the hole 10 or with the bight 7. The leg 8" is itself formed with an bar-shaped insert 8''' that itself is formed with a pair of circular holes 2. A seat 11 for the insert 8''' is formed in the leg 8" and this seat is formed with grooves 12 in which can ride tabs 13 of the insert 8''' to keep it aligned parallel to the leg 8'. Thus the two screws 3' and 3" passing through the leg 8" can shift toward and away from the two screws 3' and 3" passing through the other leg 8' for length adjustment of the assembly 1 as described below.

It can furthermore be seen from the drawing that the plate assembly 1 is associated with an brace bar or plate 14 for fastening to the legs 8' and 8", which plate can be used to bridge the space between the legs 8' and 8", the result of which is that the plate assembly 1 is greatly strengthened. Formed in the legs 8' and 8" are seats 16 into which the brace bar 14 can be inserted in a positive fit. Moreover, the brace bar 14 is formed at one end with a circular hole 2, at the other end with an elongated hole or slot 15'. The slot 15' extends in use parallel to the inner hole or slot 9 for the above-mentioned length adjustability of the assembly 1 and the central hole 15" serves merely to allow the surgeon to view the surgical site better, and also of course to allow bone and such to grow through the assembly 1.

Figure 6:
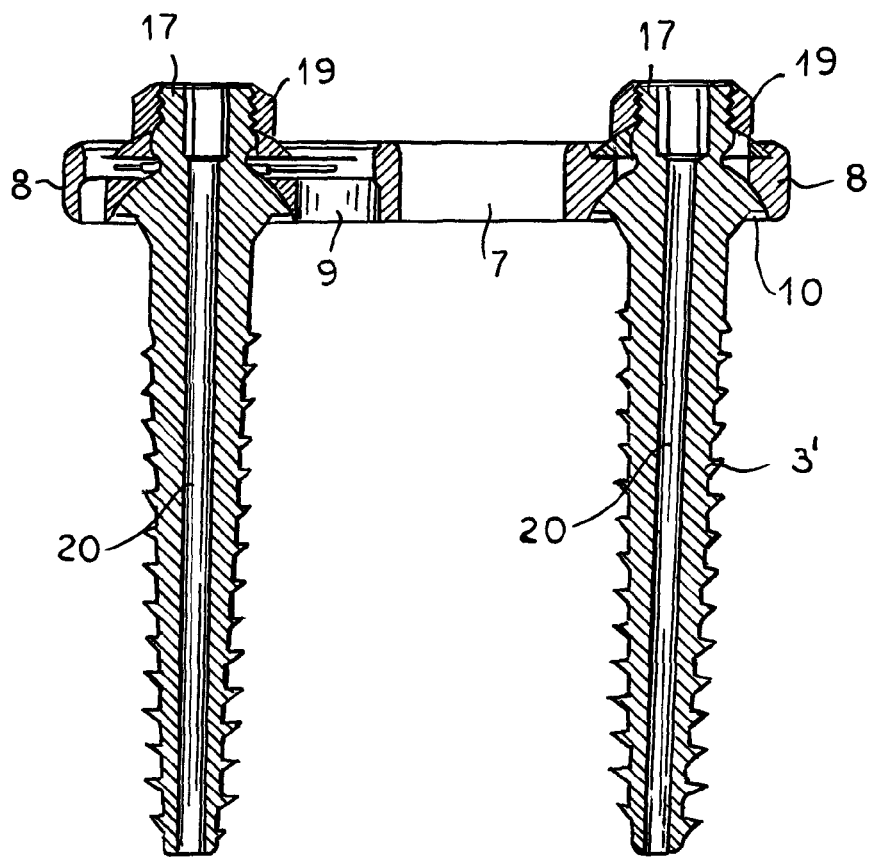
FIG. 6 is a section taken along line VI-VI of FIG. 5.
Figure 7:
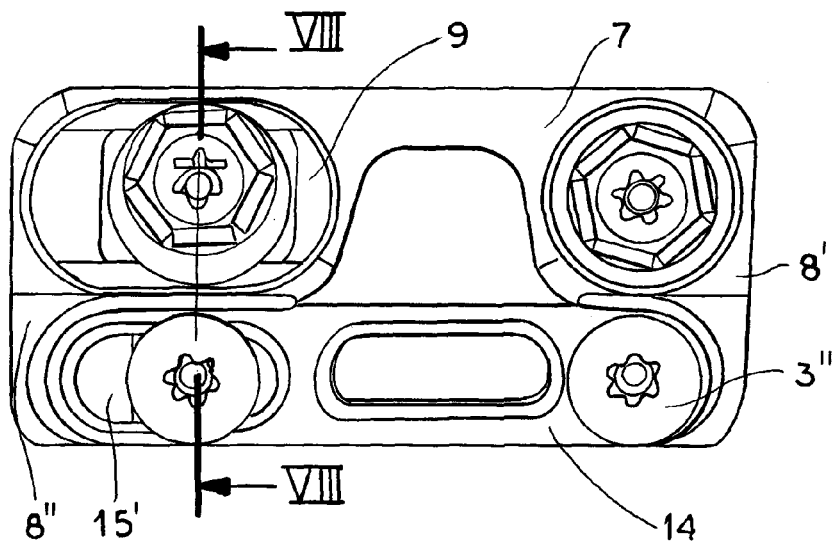
FIG. 7 is a view identical to FIG. 5.
Figure 8:
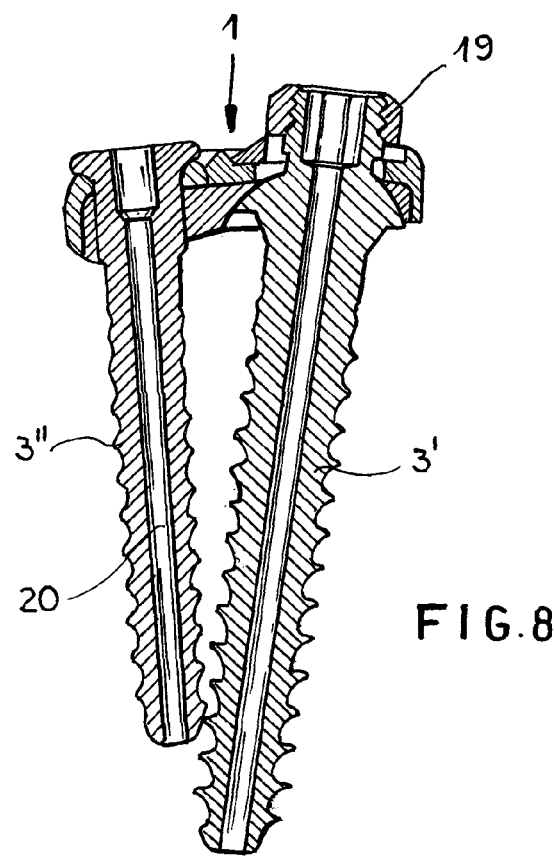
FIG. 8 is a section taken along line VIII-VIII of FIG. 7.

As can be seen from FIGS. 6 and 8, the holes 2 are part-spherically concave on the side facing the vertebra 4 so that as a result the bone screws 3' with the complementary head formations can fit in the holes 2.

Figure 9:
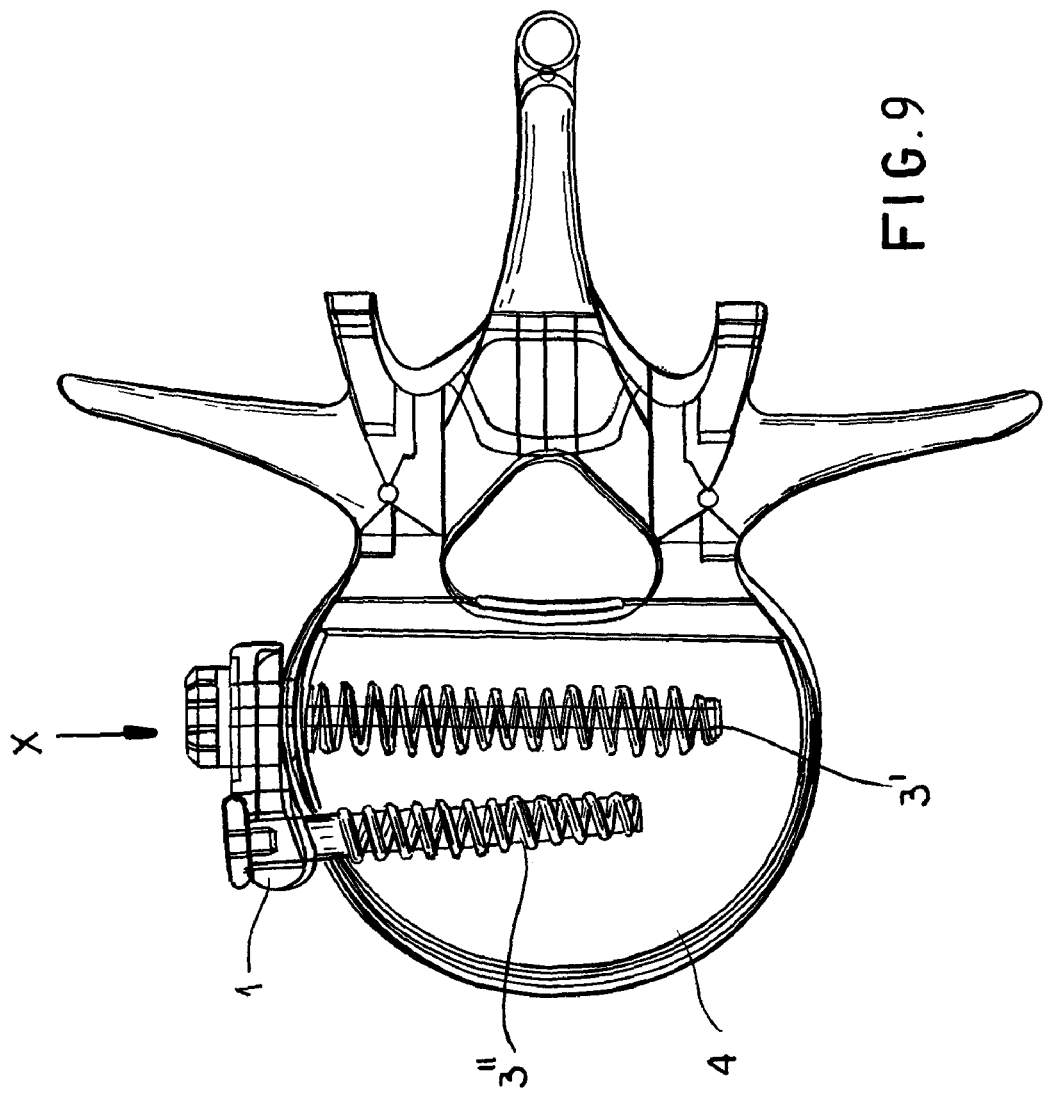
FIG. 9 is a horizontal section through a vertebra with the plate of this invention.
Figure 10:
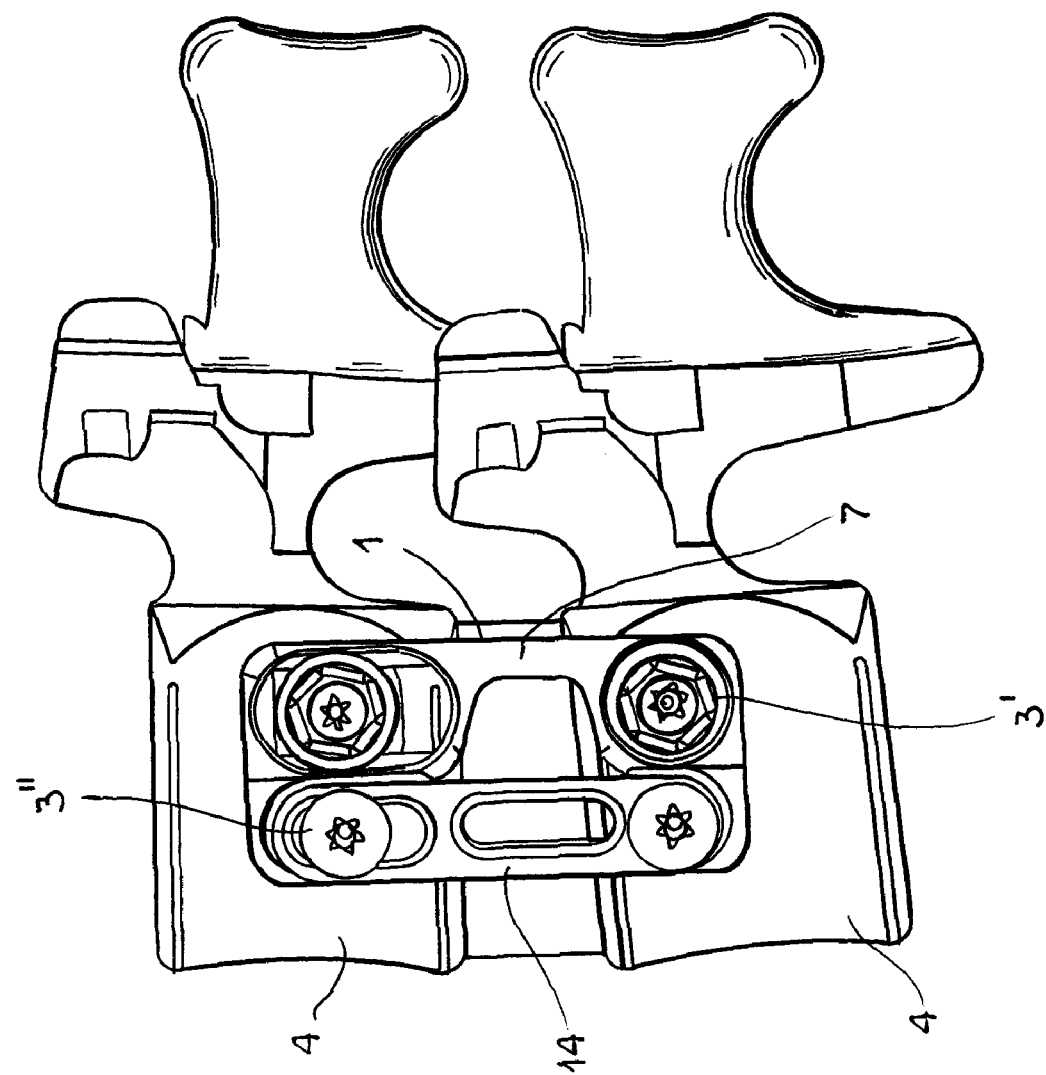
FIG. 10 is a side view taken in the direction of arrow X of FIG. 9.

FIGS. 9 through 11 show the inventive plate assembly 1 in installed condition attached laterally to two vertebral bodies 4 of a spinal column. It is possible for the surgeon first to screw the bone screws 3' with the convex head formations s into the two adjacent vertebras and then to temporarily or permanently place or secure the legs 8' and 8" and the bight 7 by means of nuts 19 threaded to the outsides of their heads 18. Because of the U-shaped configuration, access between the two vertebral bodies 4 and visibility are retained so that the surgeon also has the opportunity to fit an extensible distractor 16 between the vertebral bodies 4 as a disk replacement. Given appropriate longitudinal extension of the plate assembly 1 for bridging the gap formed by a vertebral body 4 that has been removed, it is also possible to insert a vertebral replacement body between the correspondingly spaced adjacent vertebral bodies 4. Finally, the brace bar 14 is placed into the seats 16 of the leg 8' and 8" and attached by means of the bone screws 3" with the heads 5.

FIGS. 6 and 8 indicate that the bone screws 3' and 3" are each formed with a central axially throughgoing passage 20 so an adhesive, in particular bone cement, can be forced through them for improving the seat of the bone screws 3' and 3" in the vertebral body 4. The outlet from the passage 20 does not have to be axial, but rather can also be radial.

We claim:

1. A ventral bone-plate assembly for fixation of spinal vertebras, the assembly comprising:
    a U-shaped base having a pair of longitudinally extending legs bridged by a transversely extending bight unitarily formed with and extending transversely between the legs;
    an insert juxtaposed with one of the legs and extending longitudinally from the bight at a transverse spacing from the other of the legs, the other leg and the insert each being formed at the bight with an inner hole and at a respective outer end spaced longitudinally from the respective inner hole with a respective outer hole;
    a brace bar extending transversely between the outer ends and formed with end holes alignable with the outer holes; and
    respective inner and outer bone screws, the inner screws extending through the inner holes and the outer screws each extending through a respective one of the outer holes and a respective one of the end holes.

2. The ventral bone-plate assembly defined in claim 1 wherein the bight is formed with a seat complementary fitting with the insert.

3. The ventral bone-plate assembly defined in claim 2 wherein the inner hole at the one leg is formed as a slot elongated parallel to the bight and the insert is shiftable in the seat parallel to the slot.

4. The ventral bone-plate assembly defined in claim 3 wherein the bight and insert are formed with complementary interfitting formations permitting shifting of the insert toward and away from the other leg and maintaining the insert parallel to the other leg.

5. The ventral bone-plate assembly defined in claim 1 wherein the outer ends of the legs are formed with seats in which fit ends of the brace bar.

6. The ventral bone-plate assembly defined in claim 1 wherein each of the holes has an inner face forming a part-spherical seat, each of the screws having a complementary part-spherical head formation.

7. The ventral bone-plate assembly defined in claim 1 wherein each of the screws is formed with a central longitudinally throughgoing passage through which bone cement can be forced.

8. A ventral bone-plate assembly for fixation of spinal vertebras, the assembly comprising:
    a U-shaped base having a pair of longitudinally extending legs bridged by a transversely extending bight unitarily formed with and extending transversely between the legs;
    an insert juxtaposed with one of the legs and extending longitudinally from the bight at a transverse spacing from the other of the legs, the other leg and the insert each being formed at the bight with an inner hole and at a respective outer end spaced longitudinally from the bight with an outer hole, the one leg being formed with a seat in which the insert fits, the bight being formed at the inner hole of the one leg with a slot elongated transversely and parallel to the bight, the inner hole of the one insert being a generally circular hole, the insert being transversely shiftable in the seat parallel to the slot;
    a brace bar extending transversely between the outer ends and formed with end holes alignable with the outer holes, the end hole alignable with the outer hole of the insert being formed as a slot parallel to the slot of the bight; and respective inner and outer bone screws, the inner screws extending through the inner holes and the outer screws each extending through a respective one of the outer holes and a respective one of the end holes, the screws of the one leg also extending through the slots of the bight and of the brace bar.

9. The ventral bone-plate assembly defined in claim 8 wherein each of the screws is formed with a central longitudinally throughgoing passage through which bone cement can be forced.

* * * * *